US006246904B1

(12) United States Patent
Murdock

(10) Patent No.: US 6,246,904 B1
(45) Date of Patent: Jun. 12, 2001

(54) ELECTROTRANSPORT DRUG DELIVERY RESERVOIRS CONTAINING INERT FILLERS

(75) Inventor: Thomas O. Murdock, Vadnais Heights, MN (US)

(73) Assignee: ALZA Corporation, Mountain View, CA (US)

( * ) Notice: Subject to any disclaimer, the term of this patent is extended or adjusted under 35 U.S.C. 154(b) by 0 days.

(21) Appl. No.: 08/965,881

(22) Filed: Nov. 7, 1997

Related U.S. Application Data

(60) Provisional application No. 60/033,102, filed on Dec. 17, 1996.

(51) Int. Cl.$^7$ .................................................... A61N 1/30
(52) U.S. Cl. ............................................................. 604/20
(58) Field of Search ........................ 604/20–22; 424/449, 424/448; 264/494

(56) References Cited

U.S. PATENT DOCUMENTS

| | | | |
|---|---|---|---|
| 4,164,226 | 8/1979 | Tapper | 128/419 R |
| 4,239,046 | 12/1980 | Ong | 128/650 |
| 4,524,064 | 6/1985 | Nambu | 424/81 |
| 4,664,857 | 5/1987 | Nambu | 264/28 |
| 4,731,926 | 3/1988 | Sibalis | 29/877 |
| 4,734,097 | 3/1988 | Tanabe et al. | 623/11 |
| 4,752,285 | 6/1988 | Petelenz et al. | 604/20 |
| 4,786,277 | * 11/1988 | Powers et al. | |
| 4,808,353 | 2/1989 | Nambu et al. | 264/28 |
| 4,856,188 | 8/1989 | Sibalis | 29/877 |
| 4,883,457 | 11/1989 | Sibalis | 604/20 |
| 4,925,603 | 5/1990 | Nambu | 264/28 |
| 4,988,771 | 1/1991 | Takeuchi et al. | 525/276 |
| 4,989,607 | 2/1991 | Keusch et al. | 128/640 |
| 5,002,527 | 3/1991 | Reller et al. | 604/20 |
| 5,053,001 | 10/1991 | Reller et al. | 604/20 |
| 5,080,646 | 1/1992 | Theeuwes et al. | 604/20 |
| 5,141,973 | 8/1992 | Kobayashi et al. | 523/300 |
| 5,143,071 | 9/1992 | Keusch et al. | 128/640 |
| 5,147,296 | 9/1992 | Theeuwes et al. | 604/20 |
| 5,167,617 | 12/1992 | Sibalis | 604/20 |
| 5,169,382 | 12/1992 | Theeuwes et al. | 604/20 |
| 5,169,383 | 12/1992 | Gyory et al. | 604/20 |

(List continued on next page.)

FOREIGN PATENT DOCUMENTS

| | | |
|---|---|---|
| 410009 | 5/1934 | (GB) . |
| WO 81/00785 | 3/1981 | (WO) . |

OTHER PUBLICATIONS

Kirk–Othmer, 4th Ed., vol. 11, Wiley & Sons (1994), pp 730–763, "Foamed Plastics".
Encyclopedia of Polymer Science and Engineering, vol. 7, (1987) "Gels", pp 514–531.
Encyclopedia of Polymer Science and Engineering, vol. 4, "Cross–Linking, Reversible", pp 395–417.
Encyclopedia of Polymer of Science and Engineering, vol. 4, "Cross–Linking", pp 350–395.
Encyclopedia of Polymer Science and Engineering, vol. 4, "Cross–Linking with Radiation", pp 418–449.
Gehrke, Stevin H. and Lee, Ping I, Specialized Drug Delivery Systems, Chapter 8, pp 333–392.
Encyclopedia of Pharmaceutical Technology, vol. 7, pp 441–465, "Hydrogels".

*Primary Examiner*—Manuel Mendez
(74) *Attorney, Agent, or Firm*—Owen J. Bates; Steven F. Stone

(57) ABSTRACT

A novel electrotransport drug delivery system (10) and therapeutic agent-containing reservoir (26, 28) for use therein are provided. An inert filler material effective to reduce the quantity of therapeutic agent otherwise present is incorporated in the reservoir (26, 28) along with the therapeutic agent to be delivered via electrotransport. Methods for making the reservoir (26, 28) and drug delivery system (10) are provided as well.

31 Claims, 1 Drawing Sheet

U.S. PATENT DOCUMENTS

| | | | |
|---|---|---|---|
| 5,279,543 | 1/1994 | Glikfeld et al. | 604/20 |
| 5,302,172 | 4/1994 | Sage, Jr. et al. | 604/20 |
| 5,318,514 | 6/1994 | Hofmann | 604/20 |
| 5,354,790 | 10/1994 | Keusch et al. | 523/300 |
| 5,356,632 | 10/1994 | Gross et al. | 424/449 |
| 5,358,483 | 10/1994 | Sibalis | 604/20 |
| 5,362,307 | 11/1994 | Guy et al. | 604/20 |
| 5,370,115 | 12/1994 | Ogawa et al. | 128/639 |
| 5,374,241 | 12/1994 | Lloyd et al. | 604/20 |

* cited by examiner

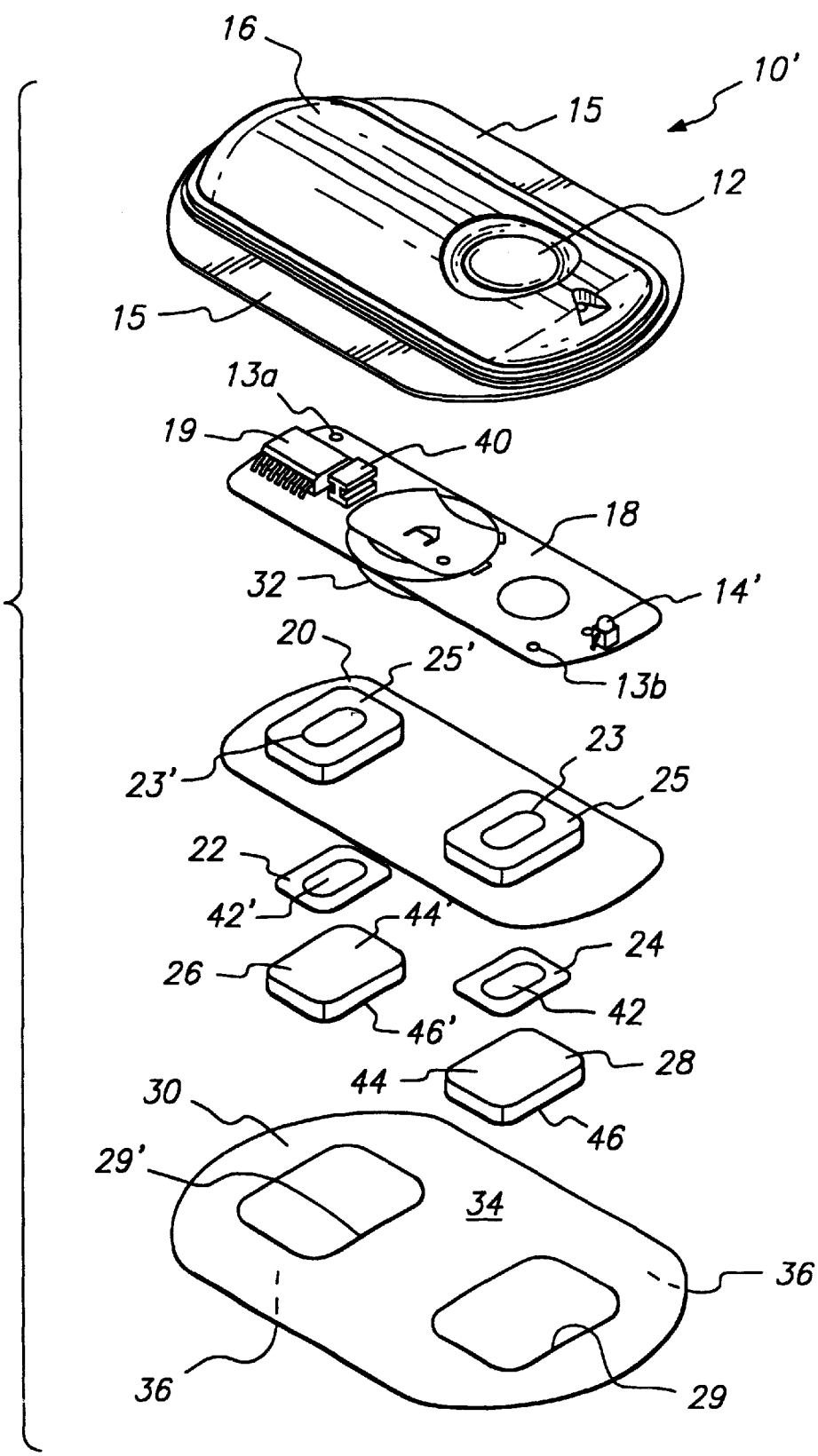

ELECTROTRANSPORT DRUG DELIVERY RESERVOIRS CONTAINING INERT FILLERS

CROSS REFERENCE TO RELATED APPLICATIONS

Applicant claims priority under 35 USC 119(e) based upon the earlier filed co-pending provisional application filed on Dec. 17, 1996, Ser. No. 60/033,102, now abandoned.

TECHNICAL FIELD

This invention relates generally to electrotransport drug delivery. More particularly, the invention relates to a method for making a new type of drug reservoir for incorporation into an electrotransport drug delivery system. The invention additionally relates to novel drug reservoirs and to electrotransport drug delivery systems containing these reservoirs.

BACKGROUND ART

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences—e.g., gastrointestinal irritation and the like—are eliminated as well. Transdermal drug delivery also makes possible a high degree of control over blood concentrations of any particular drug.

However, many drugs are not suitable for passive transdermal drug delivery because of their size, ionic charge characteristics and hydrophilicity. One method of overcoming this limitation in order to achieve transdermal administration of such drugs is the use of electrical current to actively transport drugs into the body through intact skin. The method of the invention relates to such an administration technique, i.e., to "electrotransport" or "iontophoretic" drug delivery.

Herein the terms "electrotransport", "iontophoresis", and "iontophoretic" are used to refer to the transdermal delivery of pharmaceutically active agents by means of an applied electromotive force to an agent-containing reservoir. The agent may be delivered by electromigration, electroporation, electroosmosis or any combination thereof. Electroosmosis has also been referred to as electrohydrokinesis, electroconvection, and electrically induced osmosis. In general, electroosmosis of a species into a tissue results from the migration of solvent in which the species is contained, as a result of the application of electromotive force to the therapeutic species reservoir, i.e., solvent flow induced by electromigration of other ionic species. During the electrotransport process, certain modifications or alterations of the skin may occur such as the formation of transiently existing pores in the skin, also referred to as "electroporation". Any electrically assisted transport of species enhanced by modifications or alterations to the body surface (e.g., formation of pores in the skin) are also included in the term "electrotransport" as used herein. Thus, as used herein, the terms "electrotransport", "iontophoresis" and "iontophoretic" refer to (1) the delivery of charged drugs or agents by electromigration, (2) the delivery of uncharged drugs or agents by the process of electroosmosis, (3) the delivery of charged or uncharged drugs by electroporation, (4) the delivery of charged drugs or agents by the combined processes of electromigration and electroosmosis, and/or (5) the delivery of a mixture of charged and uncharged drugs or agents by the combined processes of electromigration and electroosmosis.

Systems for delivering ionized drugs through the skin have been known for some time. British Patent Specification No. 410,009 (1934) describes an iontophoretic delivery device which overcame one of the disadvantages of the early devices, namely, the need to immobilize the patient near a source of electric current. The device was made by forming, from the electrodes and the material containing the drug to be delivered, a galvanic cell which itself produced the current necessary for iontophoretic delivery. This device allowed the patient to move around during drug delivery and thus required substantially less interference with the patient's daily activities than previous iontophoretic delivery systems.

Present electrotransport devices use at least two electrodes. Both of these electrodes are disposed so as to be in intimate electrical contact with some portion of the skin of the body. One electrode, called the active or donor electrode, is the electrode from which the drug is delivered into the body. The other electrode, called the counter or return electrode, serves to close the electrical circuit through the body. In conjunction with the patient's skin, the circuit is completed by connection of the electrodes to a source of electrical energy, e.g., a battery, and usually to circuitry capable of controlling current passing through the device. If the ionic substance to be driven into the body is positively charged, then the positive electrode (the anode) will be the active electrode and the negative electrode (the cathode) will serve as the counter electrode, completing the circuit. If the ionic substance to be delivered is negatively charged, then the cathodic electrode will be the active electrode and the anodic electrode will be the counter electrode.

Existing electrotransport devices additionally require a reservoir or source of the pharmaceutically active agent which is to be delivered or introduced into the body. Such drug reservoirs are connected to the anode or the cathode of the electrotransport device to provide a fixed or renewable source of one or more desired species or agents.

Thus, an electrotransport device or system, with its donor and counter electerodes, may be thought of as an electrochemical cell having two electrodes, each electrode having an associated half cell reaction, between which electrical current flows. Electrical current flowing through the conductive (e.g., metal) portions of the circuit is carried by electrons (electronic conduction), while current flowing through the liquid-containing portions of the device (i.e., the drug reservoir in the donor electrode, the electrolyte reservoir in the counter electrode, and the patient's body) is carried by ions (ionic conduction). Current is transferred from the metal portions to the liquid phase by means of oxidation and reduction charge transfer reactions which typically occur at the interface between the metal portion (e.g., a metal electrode) and the liquid phase (e.g., the drug solution). A detailed description of the electrochemical oxidation and reduction charge transfer reactions of the type involved in electrically assisted drug transport can be found in electrochemistry texts such as J. S. Newman, *Electrochemical Systems* (Prentice Hall, 1973) and A. J. Bard and L. R. Faulkner, *Electrochemical Methods, Fundamentals and Applications* (John Wiley & Sons, 1980).

Generally, for transdermnal drug delivery, it is preferred that drug flux be independent of the concentration of drug in the reservoirs. Concentration-independent drug flux typically occurs above a threshold concentration level; accordingly, it is desirable to maintain a higher drug concentration in the drug reservoir.

With respect to more costly drugs, such as peptides and proteins produced from genetically engineered cell lines, and/or highly potent drugs for which a very low dosage may be efficacious, it is also desirable to minimize the amount of drug loaded into the reservoir. Although it is possible to maintain the drug concentration above the threshold level required for concentration-independent drug flux by reducing both the drug loading and the volume of the reservoir, there are limitations on how small the drug reservoir may be. For example, reducing the volume of the donor reservoir by reducing the skin contact area increases the potential for skin irritation, i.e., irritation caused by the applied electric current and/or components of the drug composition delivered to the skin. Further, if the volume of the donor reservoir is reduced by decreasing the thickness of the reservoir, the potential for electrical shorting between the electrodes and the skin increases; thinner reservoirs also are inherently more difficult to manufacture with precise uniformity.

Thus, there is a need in the art for a method of minimizing drug loading in an electrotransport donor reservoir while nevertheless maintaining the drug concentration above a level required for concentration-independent drug flux, without reducing reservoir size or volume. The present invention addresses this need, and is directed to novel drug reservoirs for use in conjunction with an electrotransport drug delivery system and methods of making these new reservoirs. In contrast to prior methods for making drug reservoirs for use in electrotransport drug delivery systems, the present invention provides a reservoir that enables smaller quantities of drug to be loaded into the system, by virtue of an inert filler material dispersed throughout the drug reservoir.

DESCRIPTION OF THE INVENTION

Accordingly, the invention in one aspect is an electrotransport device which overcomes the above-mentioned limitations in the art.

It is another aspect of the invention to provide an electrotransport device for delivering a therapeutic agent through an animal body surface while minimizing the quantity of therapeutic agent contained within the device.

It is a further aspect of the invention to provide an electrotransport device which incorporates a therapeutic agent-containing polymeric reservoir comprising a polymeric matrix containing a therapeutic agent and an inert filler material.

It is still a further aspect of the invention to provide an electrotransport drug delivery device capable of cost-effectively delivering therapeutic agents such as peptides, proteins, or fragments thereof.

It is still another aspect of the invention to provide a therapeutic agent-containing polymeric reservoir for incorporation into an electrotransport device for effectively delivering a therapeutic agent through an animal body surface while minimizing the quantity of therapeutic agent contained within the reservoir.

It is a further aspect of the invention to provide a method for minimizing the quantity of therapeutic agent in a therapeutic agent-containing polymer reservoir for incorporation into an electrotransport device.

Additional aspects, advantages and novel features of the invention will be set forth in part in the description which follows, and in part will become apparent to those skilled in the art upon examination of the following, or may be learned by practice of the invention.

BRIEF DESCRIPTION OF THE DRAWING

FIG. 1 is a perspective exploded view of one embodiment of an electrotransport drug delivery system which may be used in conjunction with drug formulations made using the inventive method.

MODES FOR CARRYING OUT THE INVENTION

Before describing the present invention in detail, it is to be understood that this invention is not limited to particular drugs, carriers, electrotransport delivery systems, or the like, as such may vary.

It must be noted that, as used in this specification and the appended claims, the singular forms "a", "an" and "the" include plural referents unless the context clearly dictates otherwise. Thus, for example, reference to "a drug" or "a therapeutic agent" includes a mixture of two or more drugs or agents, reference to "an inert filler" includes two or more such fillers, and the like.

Unless defined otherwise, all technical and scientific terms used herein have the same meaning as commonly understood by one of ordinary skill in the art to which the invention pertains. Although any methods and materials similar equivalent to those described herein can be used in the practice for testing of the present invention, the preferred materials and methods are described herein.

In describing and claiming the present invention, the following specific terminology will be used in accordance with the definitions set out below.

By the terms "therapeutic agent," "drug" or "pharmaceutically active agent" as used herein is meant any chemical material or compound which induces a desired local or systemic therapeutic effect, and is capable of being delivered by electrotransport. Examples of such substances will be set forth below.

The term "inert filler material" refers to a material having substantially no tendency to interact with the therapeutic agent, by which is intended to mean that such an inert filler material will not bind, absorb, adsorb or react chemically with any significant quantity of therapeutic agent. The material will generally be particulate or fibrous, or it may be comprised of a glass bead, polymeric mesh or the like, as will be explained in detail below.

By "polymer matrix" is intended to refer to a solution of a polymer in an appropriate solvent, a solvent-containing polymer that has swollen by absorption or adsorption of the solvent, a composition comprising a dispersed, solvent-containing polymer phase combined with a continuous, solvent phase to form a viscous, colloidal composition, or other form of polymer matrix that has the chemical and/or physical characteristics that allow the incorporation of drug therein and use as a reservoir in an electrotransport drug delivery system (e.g., viscosity, surfactant properties, and the like).

A "hydrogel" is a polymer useful for forming the aforementioned polymeric matrices and capable of absorbing at least about 20 wt. % water.

In a first embodiment, then, a novel electrotransport drug delivery device is provided, the device effectively delivering a therapeutic agent through an animal body surface while minimizing the quantity of therapeutic agent contained within the drug reservoir of the device. More specifically, the electrotransport device incorporates a therapeutic agent-containing polymer reservoir having a predetermined volume (V), the reservoir comprising a polymer matrix with a predetermined quantity (q) of a therapeutic agent dispersed therein and an amount of an inert filler material effective to achieve a concentration (ρ) of the therapeutic agent in the polymer matrix which exceeds q/V. This therapeutic agent-containing polymer reservoir is also novel and represents an additional aspect of the presently claimed invention.

The inert filler material thus provides for a desired concentration of the therapeutic agent in the drug reservoir, and thus, in turn, maintains the flux of the therapeutic agent. Drug concentration can be reduced without compromising the size of the drug reservoir.

Materials suitable for use as the inert filler include, but are not limited to: glass beads; mineral filler materials, such as titanium dioxide, talc, quartz powder, or mica; and polymer filler materials. Examples of polymer filler materials are: polymer meshes, such as Saati polypropylene mesh; polymer powders having particle sizes of between about 1 μm to about 150 μm, such as micronized polymer waxes of polyethylene (e.g., Aqua Poly 250), polypropylene (e.g., Propyltex® 140S), polytetrafluoroethylene (e.g., Fluo 300), Fischer-Tropsch waxes (e.g., MP-22C, available from Micro Powders, Inc.), and mixtures thereof; crosslinked polymer beads, such as styrene/divinylbenzene (e.g., Amberlite® XAD-4 1090 or Amberlite® XAD 16-1090), acrylic/divinylbenzene (e.g., Amberlite® XAD-7) (available from Rohm and Haas), or the like; cellulosic polymers, such as crosslinked dextrans (e.g., Sephadex®) (available from Pharmacia Laboratories); polymer solids having weight average molecular weights between about 20,000, and about 225,000, such as polyvinyl alcohol (e.g., Airvol® 103, available from Air Products; Mowiol® 4-98 and Mowiol® 66-100, available from Hoechst), polyvinylpyrrolidone (e.g., Povidone PVP K-29/32; International Specialty Products), polyethylene oxide (Union Carbide), hydroxypropyl cellulose Aqualon), hydroxyethyl cellulose (Union Carbide), andmixtures thereof.

The drug reservoir is a polymeric matrix which generally although not necessarily is comprised of a hydrogel. Suitable polymers useful for forming hydrogel reservoirs include: polyvinyl alcohols; polyvinyl-pyrrolidone; cellulosic polymers, e.g., hydroxyethyl cellulose, hydroxypropyl cellulose, hydroxypropyl methylcellulose, carboxymethyl cellulose, and the like; polyurethanes; polyethylene oxides; polyanhydrides; polyvinyl pyrrolidone/vinyl acetate copolymers, and the like; and mixtures and copolymers thereof.

Therapeutic agents useful in connection with the novel reservoirs and delivery devices of the invention include any pharmaceutical compound or chemical that is capable of being delivered by electrotransport. In general, this includes agents in all of the major therapeutic areas including, but not limited to, anti-infectives such as antibiotics and antiviral agents, analgesics including fentanyl, sufentanil, buprenorphine and analgesic combinations, anesthetics, anorexics, antiarthritics, antiasthmatic agents such as terbutaline, anticonvulsants, antidepressants, antidiabetic agents, antidiarrheals, antihistamines, anti-inflammatory agents, antimigraine preparations, antimotion sickness preparations such as scopolamine and ondansetron, antinauseants, antineoplastics, antiparkinsonism drugs, antipruritics, antipsychotics, antipyretics, antispasmodics, including gastrointestinal and urinary anticholinergics, sympathomimetrics, xanthine derivatives, cardiovascular preparations including calcium channel blockers such as nifedipine, beta-blockers, beta-agonists such as dobutamine and ritodrine, antiarrythmics, anthypertensives such as atenolol, ACE inhibitors such as rinitidine, diuretics, vasodilators, including general, coronary, peripheral and cerebral, central nervous system stimulants, cough and cold preparations, decongestants, diagnostics, hormones such as parathyroid hormone, bisphosphoriates, hypnotics, immunosuppressives, muscle relaxants, parasympatholytics, parasympathomimetrics, prostaglandins, psychostimulants, sedatives and tranquilizers. The invention is particularly useful in conjunction with the electrotransport delivery of proteins, peptides and fragments thereof, whether naturally occurring, chemically synthesized or recombinantly produced.

With respect to the delivery of peptides, polypeptides, proteins and other such species, these substances typically have a weight average molecular weight of at least about 300 daltons, and more typically have a molecular weight in the range of about 300 to 40,000 daltons. Specific examples of peptides and proteins in this size range include, without limitation, GHRH, GHRF, insulin, insultropin, calcitonin, octreotide, endorphin, TRH, NT-36 (N[[(s)-4-oxo-2-azetidinyl]carbonyl]-L-histidyl-L-prolinamide), liprecin, pituitary hormones (e.g., HGH, HMG, desmopressin acetate, etc), follicle luteoids, αANF, growth factors such as growth factor releasing factor (GFRF), βMSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, HCG, hirulog, hyaluronidase, interferon, interleukins, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, bradykinin antagonists, CD4, ceredase, CSI's, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonists analogs, alpha-1 antitrypsin (recombinant), and TGF-beta.

Luteinizing hormone-releasing hormone ("LHRH") and LHRH analogs such as goserelin, buserelin, gonadorelin, napharelin and leuprolide, represent another class of peptides and proteins in this size range that are useful in connection with the present invention. One preferred LHRH analog is goserelin. Goserelin is a synthetic decapeptide analogue of LHRH having the chemical structure pyro-Glu-His-TrpSer-Tyr-DSer(But)-Leu-Arg-Pro-Azgly-$NH_2$. The drug is useful in the treatment of prostate and breast cancers and in treating certain gynecological disorders.

The therapeutic agent-containing polymer reservoir is prepared by incorporating predetermined amounts of a therapeutic agent and an inert filler material into a polymeric matrix. The polymeric matrix is typically, although not necessarily, an aqueous solution, preferably containing between about 1 wt. % to 50 wt. % polymer. The inert filler typically accounts for up to about 60 vol. %, preferably 5 to 60 vol. %, more preferably 20 to 60 vol. %, and most preferably 40 to 60 vol. % of the polymer reservoir. A relatively small quantity of the therapeutic agent, between about 0.001 wt. % to about 10 wt. %, preferably 0.01 wt. % to about 3 wt. %, and more preferably about 0.1 wt. % to about 2 wt. % of total admixture, is all that is typically used in this invention.

The incorporation of the therapeutic agent and the inert filler material into the polymeric matrix may be accomplished by any method known in the art, such as overhead stirring, double planetary mixing, Brabender mixing, volumetric metering pump, extrusion dispensing, or the like.

The therapeutic agent may be incorporated first into the polymeric matrix, followed by incorporation of the inert filler material into the therapeutic-agent containing polymeric matrix to form a therapeutic agent-containing polymeric reservoir which may then be used in an electrotransport drug delivery system. Alternatively, the inert filler material may be incorporated first into the polymeric matrix, followed by addition of the therapeutic agent into the inert filler-containing polymeric matrix. The method of this invention may in the alternative involve simultaneously incorporating the therapeutic agent and the inert filler material into the polymeric matrix.

FIG. 1 illustrates a representative electrotransport delivery device that may be used in conjunction with the present drug reservoirs. Device 10 comprises an upper housing 16, a circuit board assembly 18, a lower housing 20, anode electrode 22, cathode electrode 24, anode reservoir 26, cathode reservoir 28 and skin-compatible adhesive 30. Upper housing 16 has lateral wings 15 which assist in holding device 10 on a patient's skin. Upper housing 16 is preferably composed of an injection moldable elastomer (e.g., ethylene vinyl acetate). Printed circuit board assembly 18 comprises an integrated circuit 19 coupled to discrete components 40 and battery 32. Circuit board assembly 18 is attached to housing 16 by posts (not shown in FIG. 1) passing through openings 13a and 13b, the ends of the posts being heated/melted in order to heat stake the circuit board assembly 18 to the housing 16. Lower housing 20 is attached to the upper housing 16 by means of adhesive 30, the upper surface 34 of adhesive 30 being adhered to both lower housing 20 and upper housing 16 including the bottom surfaces of wings 15.

Shown (partially) on the underside of circuit board assembly 18 is a button cell battery 32. Other types of batteries may also be employed to power device 10.

The device 10 is generally comprised of battery 32, electronic circuitry 19,40, electrodes 22,24, and polymeric drug reservoirs 26,28, all of which are integrated into a self-contained unit. The outputs (not shown in FIG. 1) of the circuit board assembly 18 make electrical contact with the electrodes 24 and 22 through openings 23,23' in the depressions 25,25' formed in lower housing 20, by means of electrically conductive adhesive strips 42,42'. Electrodes 22 and 24, in turn, are in direct mechanical and electrical contact with the top sides 44', 44 of drug reservoirs 26 and 28. The bottom sides 46', 46 of drug reservoirs 26,28 contact the patient's skin through the openings 29', 29 in adhesive 30.

Device 10 optionally has a feature which allows the patient to self-administer a dose of drug by electrotransport. Upon depression of push button switch 12, the electronic circuitry on circuit board assembly 18 delivers a predetermined DC current to the electrode/reservoirs 22,26 and 24,28 for a delivery interval of predetermined length. The push button switch 12 is conveniently located on the top side of device 10 and is easily actuated through clothing. A double press of the push button switch 12 within a short time period, e.g., three seconds, is preferably used to activate the device for delivery of drug, thereby minimizing the likelihood of inadvertent actuation of the device 10. Preferably, the device transmits to the user a visual and/or audible confirmation of the onset of the drug delivery interval by means of LED 14 becoming lit and/or an audible sound signal from, e.g., a "beeper". Drug is delivered through the patient's skin by electrotransport, e.g., on the arm, over the predetermined delivery interval.

Anodic electrode 22 is preferably comprised of silver and cathodic electrode 24 is preferably comprised of silver chloride. Both reservoirs 26 and 28 are comprised of a polymeric material, generally a hydrogel, as described above. Electrodes 22,24 and reservoirs 26,28 are retained by lower housing 20.

The polymer reservoirs 26 and 28 contain drug solution and inert filler material uniformly dispersed in at least one of the reservoirs 26 and 28. Drug concentrations in the range of approximately $1 \times 10^{-4}$ M to 1.0 M or more can be used, with drug concentrations in the lower portion of the range being preferred.

The push button switch 12, the electronic circuitry on circuit board assembly 18 and the battery 32 are adhesively "sealed" between upper housing 16 and lower housing 20. Upper housing 16 is preferably composed of rubber or other elastomeric material. Lower housing 20 is preferably composed of a plastic or elastomeric sheet material (e.g., polyethylene) which can be easily molded to form depressions 25,25' and cut to form openings 23,23'. The assembled device 10 is preferably water resistant (i.e., splash proof) and is most preferably waterproof. The system has a low profile that easily conforms to the body, thereby allowing freedom of movement at, and around, the wearing site. The reservoirs 26 and 28 are located on the skin-contacting side of the device 10 and are sufficiently separated to prevent accidental electrical shorting during normal handling and use.

The device 10 adheres to the patients body surface (e.g., skin) by means of a peripheral adhesive 30 which has upper side 34 and body-contacting side 36. The adhesive side 36 has adhesive properties which assures that the device 10 remains in place on the body during normal user activity, and yet permits reasonable removal after the predetermined (e.g., 24-hour) wear period. Upper adhesive side 34 adheres to lower housing 20 and retains the electrodes and drug reservoirs within housing depression 25,25' as well as retains lower housing 20 attached to upper housing 16.

While the invention has been described in conjunction with the preferred specific embodiments thereof, it is to be understood that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

Preparation of Cellulose Acetate Inert Filler-Containing Hydrogel Polymer Reservoir Into a 250 mL jacketed glass beaker was added 59.0 g of purified water, USP. A rubber stopper equipped with a powder addition funnel, thermocouple thermometer, and a stainless steel stirring shaft with a Delrin® paddle was inserted into the mouth of the beaker. -The water was stirred with an overhead stirrer while warming to 70° C. Hydroxypropyl methylcellulose (HPMC) (Methocel K-100MP, Dow Chemical) was added to the beaker through the powder addition funnel and the mixture was stirred for 5–10 minutes to prepare a uniform dispersion of HPMC in the hot water. Poly(vinyl alcohol), 10.0 g, (Mowiol® 66–100, Hoechst Celanese) was added to the beaker through the powder addition funnel and the mixture was warmed to about 90°C. to 95° C. and held at that temperature for 70 minutes. The poly(vinyl alcohol) solution was cooled to 75° C. and 15.0 g of cellulose acetate (Aldrich Chemical) was added to the beaker in 5.0 g aliquots through the powder addition funnel and stirred for 5 to 10 minutes. The poly(vinyl alcohol) solution was cooled to 60° C. and 15.0 g of AG 3-X4 (50% HCl form) (BioRad) ion exchange resin was added to the beaker and the mixture was stirred for 5 to 10 minutes. The poly(vinyl alcohol) solution was transferred into a polypropylene syringe that had been previously warmed to 60° C. with an aluminum heating block, and the poly(vinyl alcohol) solution was dispensed with a Multicore Solder Paste Dispenser into 2.0 cm$^2$×0.16 cm foam mold hydrogel reservoirs. The filled hydrogel reservoirs were placed into a –20° C. freezer for 18 hours and then removed from the freezer and allowed to warm to 4° C. over an eight-hour interval. The hydrogel containing the cellulose acetate inert filler was subsequently used for drug delivery studies.

EXAMPLE 2

Preparation of Acrylic/Divinylbenzene Inert Filler-Containing Hydrogel Polymer Reservoir Into a 250 mL jacketed glass beaker was added 39.0 g of purified water, USP, and a rubber stopper equipped with a powder addition funnel, thermocouple thermometer, and a stainless steel stirring shaft with a Delrin® paddle was inserted into the mouth of the beaker. The water was stirred with an overhead stirrer while warming to 70° C. Hydroxypropyl methylcellulose (HPMC) (Methocel K-100MP, Dow Chemical) was added to the beaker through the powder addition funnel and the mixture was stirred for 5–10 minutes to prepare a uniform dispersion of HPMC in the hot water. Poly(vinyl alcohol), 10.0 g, (Mowiol 66–100, Hoechst Celanese) was added to the beaker through the powder addition funnel and the mixture was warmed to 90° C. to 95° C. and held at that temperature for 70 minutes. The poly (vinyl alcohol) solution was cooled to 75° C. and 35.0 g of acrylicidivinylbenzene crosslinked polymer beads (Amberlite® XAD-7; Rohm & Haas) was added to the beaker through the powder addition funnel and stirred for 5 to 10 minutes. The poly(vinyl alcohol) solution was cooled to 60° C. and 15.0 g of AG 3-X4 (50% HCl form) (BioRad) ion exchange resin was added to the beaker and the mixture was stirred for 5 to 10 minutes. The poly(vinyl alcohol) solution was transferred into a polypropylene syringe that had been previously warmed to 60° C. with an aluminum heating block and the poly(vinyl alcohol) solution was dispensed with a Multicore Solder Paste Dispenser into 2.0 cm$^2$×0.16 cm foam mold hydrogel reservoirs. The filled hydrogel reservoirs were placed into a –20° C. freezer for 18 hours and then removed from the freezer and allowed to warm to 4° C. over an eight hour interval. The hydrogel containing the Amberlite® XAD-7 inert filler was subsequently used for drug delivery studies.

EXAMPLE 3

Preparation of Inert Filler Goserelin Acetate-Containing Polymer Reservoirs

The objective of the experiment was to determine the compatibility of a goserelin acetate solution with various filler materials listed in Table 1 and to assess which materials irreversibly bind goserelin acetate.

TABLE 1

Filler Materials Screened

| Description | Trade Name | Source |
| --- | --- | --- |
| Polypropylene Mesh | Saati Mesh 980/47 | Saati |
| Micronized polyethylene wax | Propyltex 140S | Micron Powders |
| Micronized polytetrafluoroethylene | Fluo 300 | Micron Powders |
| Micronized Fischer-Tropsch wax | MP-22C | Micron Powders |
| Micronized Polyethylene wax | Aqua Poly 250 | Micron Powders |
| Titanium dioxide | Spectraspray White 50802 | Warner Franklin |
| Styrene/divinylbenzene resin | Amberlite ® XAD-4 | Rohm & Haas |
| Acrylic/divinylbenzene resin | Amberlite ® XAD-7 | Rohn & Haas |
| Styrene/divinylbenzene resin | Amberlite ® XAD16/1090 | Rohn & Haas |
| Cellulose type 20 | Sigmacell ® | Sigma |
| Dextran/epichlorohydrin | Sephadex ®G-25 | Sigma |
| Silica gel | Nucleosil ®100-10 | Phenomenex |

A 0.15 g sample of the inert filler was weighed into a polypropylene vial and 2.5 mL of HPLC-grade water was added. A cap was placed on the vial and the sample was allowed to equilibrate at ambient temperature overnight to assure that the inert filler was completely hydrated prior to the addition of the goserelin acetate solution. The vials were opened and 0.50 mL of a goserelin acetate solution was added to the sample to provide a 1.0 mg/mL solution of goserelin acetate in contact with the inert filler. The samples were placed on a shaker at ambient temperature and samples were removed after 24 hours, 72 hours, 1 week, 2 weeks, and 3 weeks and the concentration of goserelin acetate in solution was determined by HPLC assay. Control samples were prepared by adding 2.5 mL of HPLC-grade water and 0.5 mL of the goserelin acetate solution to yield a 1.0 mg/mL goserelin acetate solution. The control goserelin acetate solutions were stored at 4° C. and 25° C. and sampled at each timepoint. The HPLC analysis of the goserelin acetate solutions in contact with the inert filler after three weeks are shown in Table 2.

TABLE 2

Filler Material Screening Study with Goserelin Acetate

| Filler Material (Trade Name) | Goserelin (% Control) |
| --- | --- |
| Polypropylene Mesh (Saati Mesh 980/47) | 106.4 |
| Fluo 300 (Micronized PTFE Wax) | 89.9 |
| MP-22C (Micronized F-T Wax) | 119.3 |
| Propyltex 140S (Micronized PE Wax) | 101.8 |
| AquaPoly 250 (Micronized PE Wax) | 89.5 |
| Magnesium Silicate (123 Talc) | 70.2 |
| Titanium Dioxide (Spectraspray White 50802) | 80.6 |
| Dextran/Epichlorohydrin (Sephadex G-25) | 86.4 |
| Cellulose Type 20 (Sigmacell ®) | 70.1 |
| Cellulose Acetate | 108.5 |
| Silica gel (Nucleosil ® 100-10) | 51.4 |
| Poly(vinyl alcohol) (Airvol 103) | 92.7 |

The results provided in Table 2 indicate that goserelin acetate is acceptably compatible with micronized polymeric waxes such as polyethylene and Fischer-Tropsch wax based on the HPLC assay of the samples. The polypropylene mesh and cellulose acetate were also acceptable inert fillers since essentially no loss of goserelin acetate was detected from the test solution after three weeks. Mineral fillers such as titanium dioxide (Spectraspray White 50802), silicon dioxide (Nucleosil® 100-10) and magnesium silicate (123 Talc) in contact with the goserelin acetate solution resulted in an approximately 30% to 50% loss of goserelin acetate from the test solution after three weeks. Amberlite® XAD resins in contact with the goserelin acetate test solution resulted in 0% recovery of goserelin acetate after 24 hours.

What is claimed is:

1. An electrotransport agent delivery device, comprising a donor electrode, a counter electrode and a source of electrical power adapted to be electrically connected to the donor and counter electrodes, wherein the donor electrode is electrically connected to a donor reservoir having a predetermined volume (V) and being comprised of a polymeric matrix containing a predetermined quantity (q) of a therapeutic agent to be delivered, the polymeric matrix also containing an inert filler material having substantially no tendency to interact with the agent, the inert filler being present in the matrix in a form which allows electrotransport of the agent through and from the reservoir to a patient body surface, the inert filler material being present in the polymeric matrix in an amount which achieves a concentration (ρ) of therapeutic agent in the matrix which exceeds q/V.

2. The device of claim 1, wherein the polymeric matrix is comprised of a water-swellable polymer selected from the group consisting of polyvinyl alcohols, polyvinylpyrrolidone, cellulosic polymers, polyurethanes, polyethylene oxide, polyanhydrides, polyvinyl pyrrolidone/vinyl acetate copolymers, and mixtures and copolymers thereof.

3. The device of claim 1, wherein the inert filler material has substantially no tendency to bind, absorb, adsorb or react chemically with the therapeutic agent.

4. The device of claim 1, wherein the inert filler material comprises up to about 60 vol. % of the polymeric matrix.

5. The device of claim 1, wherein the inert filler material comprises about 5 vol. % to 60 vol. % of the polymeric matrix.

6. The device of claim 1, wherein the inert filler material comprises about 20 vol. % to 60 vol. % of the polymeric matrix.

7. The device of claim 1, wherein the inert filler material comprises about 40% vol. % to 60 vol. % of the polymeric matrix.

8. The device of claim 1, wherein the inert filler is in the form of solid particles or fibers dispersed in the polymeric matrix.

9. The device of claim 8, wherein the inert filler material is selected from the group consisting of glass beads, polymer powders, polymer beads, polymer solids, cellulose polymers, mineral fillers, and mixtures thereof.

10. The device of claim 1, wherein the inert filler material is comprised of a polymer mesh.

11. The device of claim 10, wherein the polymer mesh is comprised of polypropylene.

12. The device of claim 9, wherein the inert filler is comprised of a polymer powder.

13. The device of claim 12, wherein the polymer powder comprises a micronized polymer with particle size of about 1 μm to about 50 μm.

14. The device of claim 13, wherein the micronized polymer is selected from the group consisting of polyethylene waxes, polypropylene waxes, polytetrafluoroethylene waxes, Fischer-Tropsch waxes, and mixtures thereof.

15. The device of claim 9, wherein the inert material comprises beads of a crosslinked polymeric material.

16. The device of claim 15, wherein the crosslinked polymeric material is selected from the group consisting of acrylic/divinylbenzene copolymers, styrene/divinylbenzene copolymers, and mixtures thereof.

17. The device of claim 9, wherein the inert filler is comprised of a polymer solid.

18. The device of claim 17, wherein the polymer solid is selected from the group consisting of polyvinyl alcohol, polyvinylpyrrolidone, and mixtures thereof.

19. The device of claim 9, wherein the inert filler is comprised of a mineral filler material.

20. The device of claim 19, wherein the mineral filler material is selected from the group consisting of titanium dioxide, mica, quartz powder, talc, and mixtures thereof.

21. A donor reservoir for an electrotransport agent delivery device, the reservoir having a predetermined volume (V) and being comprised of a polymeric matrix containing a predetermined quantity (q) of a therapeutic agent to be delivered, the polymeric matrix also containing an inert filler material having substantially no tendency to interact with the agent, the inert filler being present in the matrix in a form which allows electrotransport of the agent through and from the reservoir to a patient body surface, the inert filler material being present in the polymeric matrix in an amount which achieves a concentration (ρ) of therapeutic agent in the matrix which exceeds q/V.

22. The reservoir of claim 21, wherein the polymer matrix comprises a water-swellable polymer selected from the group consisting of polyvinyl alcohols, polyvinyl pyrrolidone, cellulosic polymers, polyurethanes, polyethylene oxide, polyanhydrides, polyvinyl pyrrolidone/vinyl acetate copolymers, and mixtures and copolymers thereof.

23. The reservoir of claim 21, wherein the inert filler material has substantially no tendency to bind, absorb, adsorb or react chemically with the therapeutic agent.

24. The reservoir of claim 21, wherein the inert filler material comprises up to about 60 vol. % of the polymeric matrix.

25. The reservoir of claim 21, wherein the inert filler material comprises about 5 vol. % to 60 vol. % of the polymeric matrix.

26. The reservoir of claim 21, wherein the inert filler material comprises about 20 vol. % to 60 vol. % of the polymeric matrix.

27. The reservoir of claim 21, wherein the inert filler material comprises about 40 vol. % to 60 vol. % of the polymeric matrix.

28. The reservoir of claim 21, wherein the inert filler is in the form of solid particles or fibers dispersed in the polymeric matrix.

29. The reservoir of claim 28, wherein the inert filler material is selected from the group consisting of glass beads, polymer powders, polymer beads, polymer solids, cellulose polymers, mineral fillers, and mixtures thereof.

30. The reservoir of claim 21, wherein the inert filler is comprised of a polymer mesh.

31. A method for increasing the volume (V) of a polymeric donor reservoir for an electrotransport delivery device, the reservoir containing a predetermined quantity (q) of the therapeutic agent to be delivered, without decreasing the concentration (ρ) of the therapeutic agent in the reservoir, the method comprising placing a predetermined amount of an inert filler material in a polymer matrix, the filler material having substantially no tendency to interact with the therapeutic agent, to produce a donor reservoir comprised of a drug- and inert filler-containing polymer matrix.

* * * * *